United States Patent [19]

Brown et al.

[11] Patent Number: 5,300,126
[45] Date of Patent: Apr. 5, 1994

[54] PROCESS FOR IMPROVING OLEFIN ETHERIFICATION CATALYST LIFE

[75] Inventors: Stephen H. Brown, Princeton; Quang N. Le, Cherry Hill; Lawrence B. Alemany, Swedesboro, all of N.J.

[73] Assignee: Mobil Oil Corporation, Fairfax, Va.

[21] Appl. No.: 963,955

[22] Filed: Oct. 19, 1992

[51] Int. Cl.$^5$ .............................................. C10L 1/18
[52] U.S. Cl. ..................... 44/449; 44/389; 44/403; 44/447; 568/697; 585/310; 585/311; 585/533; 585/671
[58] Field of Search ............... 585/361, 362, 311, 312, 585/313, 533, 671; 44/389, 403, 447, 449; 568/697

[56] References Cited

U.S. PATENT DOCUMENTS

| | | | |
|---|---|---|---|
| 4,128,403 | 12/1978 | Honnen | 44/403 |
| 4,525,174 | 6/1985 | Croudace | 44/403 |
| 4,605,787 | 8/1986 | Chu et al. | 568/697 |
| 4,624,682 | 11/1986 | Sung et al. | 44/419 |
| 4,774,364 | 9/1988 | Chou | 585/311 |
| 4,981,491 | 1/1991 | Harandi et al. | 44/449 |
| 5,009,670 | 4/1991 | Martischius | 44/385 |
| 5,210,326 | 5/1993 | Marquez et al. | 368/697 |

Primary Examiner—Anthony McFarlane
Attorney, Agent, or Firm—A. J. McKillop; M. D. Keen; L. Gene Wise

[57] ABSTRACT

A method is disclosed for the pretreatment of olefinic hydrocarbon feedstock to remove conjugated dienes and/or basic nitrogen compounds that deactivate acidic catalyst particles used in olefin conversion processes by reacting the dienes with one or more dienophiles to form the corresponding Diels-Alder adduct, followed by catalytic conversion of the olefinic hydrocarbon feedstock containing the adduct. The formation of the Diels-Alder adduct essentially eliminates the role of dienes in the feedstock as catalyst deactivating agents. When maleic anhydride (MA) is employed as the dienophile, basic nitrogen reacts with maleic anhydride, or with the tetrahydrophthalic anhydride adduct, to lower the amount of catalyst deactivating basic nitrogen compounds in the feedstock. Where the olefin conversion process comprises etherification of isoolefins with alkanol in a C4+ or C5+ olefinic hydrocarbon feedstream to produce a gasoline boiling range product enriched in oxygen and rich in high octane value alkyl tertiary alkyl ethers, it has been discovered that the adduct, particularly those adducts formed with MA, is in the gasoline boiling range and contributes usefully to the oxygen enrichment of the gasoline and to octane value.

34 Claims, 1 Drawing Sheet

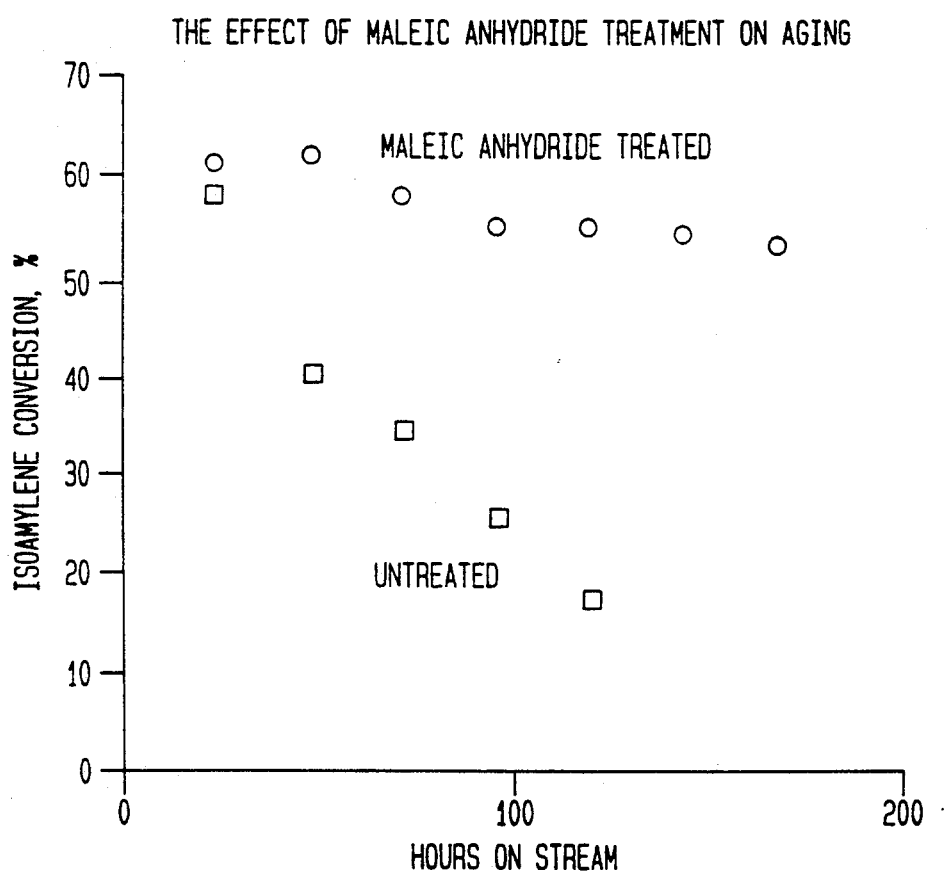

PROCESS FOR IMPROVING OLEFIN ETHERIFICATION CATALYST LIFE

This invention relates to a novel method for increasing catalyst life in processes utilizing solid acidic catalyst particles for olefin conversion processes. The invention particularly relates to a method for removing dienes and basic nitrogen that act as catalyst poisons in acidic, shape selective zeolite catalyzed olefin etherification, oligomerization, skeletal isomerization or hydration processes. The method is especially applicable to processes for etherification of isoolefins in $C_5+$ olefinic gasoline streams wherein catalyst deactivating dienes, basic nitrogen and thiophenic sulfur are removed from the feedstream by reaction with maleic anhydride or other dienophiles.

BACKGROUND OF THE INVENTION

It is known that isobutylene and isoamylenes, and other isoalkenes or isoolefins, produced by hydrocarbon cracking may be reacted with methanol and other $C_2$-$C_4$ lower aliphatic alcohols, or alkanol, over an acidic catalyst to provide methyl tertiary butyl ether (MTBE), methyl tertiary-amyl ether (TAME) or the like. Generally, it is known that asymmetrical ethers having the formula $(CH_3)_3C$—$O$—$R$, where R is a $C_1$-$C_4$ alkyl radical, are particularly useful as octane improvers for liquid fuels, especially gasoline.

MTBE, ethyl t-butyl ether (ETBE), tert-amyl methyl ether (TAME) and isopropyl t-butyl ether (IPTBE) are known to be high octane ethers. The article by J. D. Chase, et al., *Oil and Gas Journal*, Apr. 9, 1979, discusses the advantages one can achieve by using such materials to enhance gasoline octane. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114.

The liquid phase reaction of methanol with isobutylene and isoamylenes at moderate conditions with a resin catalyst is known technology, as provided by R. W. Reynolds, et al., *The Oil and Gas Journal*, Jun. 16, 1975, and S. Pecci and T. Floris, *Hydrocarbon Processing*, December 1977. An article entitled "MTBE and TAME—A Good Octane Boosting Combo," by J. D. Chase, et al., *The Oil and Gas Journal*, Apr. 9, 1979, pages 149-152, discusses the technology. Preferred catalysts are polymeric sulfonic acid exchange resin such as Amberlyst 15 and zeolites such as zeolite Beta and ZSM-5. The acid resin catalysts are effective catalysts at temperatures below 90° C. At higher temperatures the resin catalyst is unstable. Typically, with acid resin catalyst the etherification reaction is carried out in liquid phase. However, mixed phase etherification is known, particularly where the catalyst is contained as a fixed bed in a fractionator which serves to both separate the reaction products and operate as a vessel to contain the catalyst under etherification conditions. Smith U.S. Pat. No 4,978,807 describes an etherification catalyst reaction zone contained within a distillation tower.

European Patent Applications 0055045 and 0045618 describe isoolefin etherification catalyzed by zeolite. Chu et al. U.S. Pat. No. 4,605,787, incorporated herein by reference, describes a process for the preparation of methyl tertiary butyl ether which comprises reacting isobutylene and methanol in the presence of zeolite catalyst.

Typical hydrocarbon feedstock materials for etherification reactions include olefinic streams, such as cracking process light gas containing butene isomers in mixture with substantial amounts of paraffins including n-butane and isobutane. The $C_4$ components usually contain a major amount of unsaturated compounds, such as 10-40% isobutylene, 20-55% linear butenes, and small amounts of butadiene. Also, $C_4+$ heavier olefinic hydrocarbon streams may be used, particularly mixtures of isobutylene and isoamylene. $C_5+$ olefinic hydrocarbon streams containing isoamylene comprising fluid catalytic cracking (FCC) gasoline are an especially important feedstock.

Improvements in the etherification of isoamylenes to TAME in $C_5+$ FCC gasoline are very desirable to meet the amended requirements of the Clean Air Act with respect to gasoline oxygen content while avoiding $C_4-$ hydrocarbon evaporative emissions. These amendments specify that gasoline sold in CO non-attainment areas during winter months will have 2.7 wt % oxygen by 1992 while in ozone non-attainment areas 2.0 wt % year round must be achieved by 1995.

As noted above, the use of zeolite catalyst for the etherification reaction of lower alkanol with isoolefins to produce MTBE and/or TAME is well known in the art. Among the advantages in employing acidic zeolite for the catalysis of etherification is the fact that it is much more readily regenerable than acidic resin catalyst. While sulfonated resin catalysts such as Amberlyst-15 are highly effective as etherification catalysts the fact that they are organic resins limits the temperatures to which they can be exposed without degradation. Zeolites, on the other hand, are stable at high temperatures which allows the repeated regeneration of deactivated catalyst. High temperature catalyst regeneration is by far the preferred route for regeneration to remove carbonaceous deposits, particularly produced by diene contaminates in the etherification hydrocarbon feedstream.

It is known that conjugated dienes such as butadiene and higher $C_5+$ conjugated dienes readily oligomerize on the surface of acidic catalyst particles at moderate temperature forming carbonaceous deposits which accelerate catalyst deactivation. This mode of acidic solid catalyst particle deactivation is relatively generic to olefin conversion processes, particularly zeolite catalyzed etherification of olefinic gasoline streams. Consequently, pretreatment of the feedstock by hydrotreating and stripping is conventionally carried out to lower the concentration of diene in the feedstock. Basic nitrogen compounds, i.e., ammonia or amines, are also known catalyst poisons in etherification processes where they react with acid catalyst sites and lower catalyst activity. To avoid this problem, water washing of the feedstock is usually prescribed. Overall, the pretreatment of etherification feedstock to lower the rate of catalyst deactivation caused by dienes and basic nitrogen compounds represents a substantial economic burden on the etherification process.

It is an object of the present invention to provide an improved process for the removal of catalyst poisons comprising conjugated dienes, thiophenic sulfur and/or basic nitrogen compounds from olefinic hydrocarbon feedsteams used in zeolite catalyzed olefin conversion processes.

It is a particular object of the invention to provide a process for removing conjugated dienes, thiophenic sulfur and/or basic nitrogen compounds from olefinic hydrocarbon feedstreams employed in solid acid catalyzed etherification processes for the production of alkyl tertiary alkyl ethers.

Yet a further object of the invention is to provide a process for removing catalyst deactivating amounts of dienes from solid acid catalyzed olefin etherification process feedstreams that are carried out on $C_4+$ or $C_5+$ olefinic gasoline boiling range hydrocarbons.

SUMMARY OF THE INVENTION

The pretreatment of olefinic hydrocarbon feedstock to remove conjugated dienes, sulfur and/or basic nitrogen compounds that deactivate acidic catalyst particles used in olefin conversion processes can be substantially simplified by reacting the dienes, basic nitrogen compounds and/or thiophenes with one or more dienophiles to form the corresponding Diels-Alder adduct, followed by catalytic conversion of the olefinic hydrocarbon feedstock containing the adduct. The formation of the Diels-Alder adduct essentially eliminates the role of dienes in the feedstock as catalyst deactivating agents. When maleic anhydride (MA) is employed as the dienophile, basic nitrogen reacts with maleic anhydride, or with the tetrahydrophthalic anhydride adduct, to lower the amount of catalyst deactivating basic nitrogen compounds in the feedstock. Where the olefin conversion process comprises etherification of isoolefins with alkanol in a $C_4+$ or $C_5+$ olefinic hydrocarbon feedstream to produce a gasoline boiling range product enriched in oxygen and rich in high octane value alkyl tertiary alkyl ethers, it has been discovered that the adduct, particularly those adducts formed with MA, is in the gasoline range and contributes usefully to the oxygen enrichment of the gasoline and to octane value.

More particularly, a process is disclosed for improving the catalyst life in olefinic hydrocarbon feedstream conversion processes carried out in contact with catalyst particles wherein the hydrocarbon feedstream contains catalyst deactivating amounts of conjugated diene. The process comprises treating the feedstream with at least one dienophile under reaction conditions sufficient to form the adduct of the diene and dienophile whereby a reaction product is produced comprising an olefinic hydrocarbon feedstream containing a substantially lower amount of diene. The reaction product is converted in contact with catalyst particles. The catalyst particles are found to have an enhanced catalyst life.

In one embodiment the process comprises a process for the production of $C_5+$ gasoline boiling range hydrocarbons rich in alkyl tertiary alkyl ethers from a $C_5+$ olefinic hydrocarbon feedstream rich in isoolefins and containing catalyst deactivating amounts of dienes. The $C_5+$ feedstream is contacted with at least one dienophile under reaction conditions sufficient to form the adduct of the diene and the dienophile, preferably maleic anhydride, whereby a reaction product is produced comprising an olefinic hydrocarbon feedstream containing a substantially lower amount of diene. The reaction product and an alkanol feedstream are contacted with acidic etherification catalyst under isoolefin etherification conditions whereby an effluent stream is produced comprising unconverted $C_5+$ hydrocarbons, unconverted alkanol, the adduct and alkyl tertiary alkyl ether.

The invention further encompasses a novel composition of high octane value gasoline having an enhanced oxygen content. The novel composition consists of $C_5+$ gasoline boiling range hydrocarbons containing alkyl substituted tetrahydrophthalic anhydride or $C_1$-$C_4$ esters thereof.

DESCRIPTION OF THE DRAWING

The FIGURE is a graphical representation of catalyst aging using comparative etherification data on MA pretreatment of feed to remove dienes versus no diene removal pretreatment step.

DETAILED DESCRIPTION OF THE INVENTION

The present invention consists, in part, of the discovery that in petroleum refining processes Diels-Alder dienophiles can be used to remove catalyst deactivating amounts of conjugated dienes from olefinic hydrocarbon feedstreams.

Conjugated dienes are contained in a variety of olefinic hydrocarbon feedstocks used in a variety of olefin conversion processes catalyzed by solid acid particles, particularly medium and large pore shape selective zeolite catalyst particles. The high reactivity and functionality of these dienes contribute to an acceleration of catalyst aging by the formation of carbonaceous deposits on the catalyst unless the feedstock is pretreated to eliminate them. The instant invention is applicable to all such processes where the elimination of conjugated dienes by pretreatment of the hydrocarbon feedstock is a preferred prerequisite. These processes include olefin oligomerization, skeletal isomerization and hydration processes, inter alia; but, most preferably, processes employing olefin etherification of $C_4+$ or $C_5+$ olefinic hydrocarbon streams boiling in the range of gasoline.

The novel pretreatment process described herein is applicable to fixed bed and fluid bed processes employing medium pore zeolite catalyst particles for the conversion or oligomerization of light olefins to gasoline boiling range and higher molecular weight hydrocarbons (MOG and MOGD processes), dewaxing of lube stock or fuel oil (MLDW and MDDW processes) and similar metallosilicate catalyzed hydrocarbon conversion processes having in common the diene initiated deactivation of catalyst by the deposition of coke and other carbonaceous material on the catalyst surface and within the catalyst pores. These include zeolite catalyzed olefin isomerization, aromatization (M-2 Forming), and dehydrogenation. The zeolite catalyst may contain other metals such as platinum, palladium or tin.

A major development within the petroleum industry has been the discovery of the special catalytic capabilities of a family of zeolite catalysts based upon medium pore size shape selective metallosilicates. Discoveries have been made leading to a series of analogous processes drawn from the catalytic capability of zeolites. Depending upon various conditions of space velocity, temperature and pressure lower oxygenates, such as methanol, can be converted in the presence of zeolite type catalyst to olefins; olefins can catalytically oligomerize to provide gasoline or distillate or can be converted further to produce aromatics.

Conversion of olefins to gasoline and/or distillate product is disclosed in U.S. Pat. Nos. 3,960,978 and 4,021,502 (Givens, Plank and Rosinski). In Garwood et al U.S. Pat. Nos. 4,150,062 and 4,227,992 disclose the operating conditions for the Mobil Olefin to Gasoline/Distillate (MOGD) process for selective conversion of $C_3+$ olefins. A fluidized bed process for converting ethene-containing light olefinic streams in the Mobil Olefin to Gasoline (MOG) process is described by Avidan et al in U.S. patent application 006,407, filed 23 Jan. 1987. The phenomena of shape-selective polymerization are discussed by Garwood in ACS Symposium Series No. 218, Intrazeolite Chemistry, "Conversion of $C_2$–$C_{10}$ to Higher Olefins over Synthetic Zeolite ZSM-5", 1983 American Chemical Society. U.S. Pat. No. 3,827,968 (Givens et al.) discloses a two stage operation wherein a mixed feed containing paraffins and olefins is upgraded in the absence of added hydrogen to a highly aromatic gasoline product. Catalyst dewaxing of lube stock (MLDW) using zeolite catalyst such as ZSM-5 is described in U.S. Pat. Nos. 4,181,598 to Gillespie et al., 4,259,170 to Graham et al. and 4,283,271 to Garwood et al.. Dewaxing of distillate fuel oils (MDDW) is described in U.S. Pat. No. 4,419,220 to LaPierre, et al and U.S. Pat. No. 3,891,540 to Demmel et al. The foregoing patents are all of common assignee and are incorporated herein by reference in their entirety.

As noted herein before, the etherification of isoolefins with alkanol using acidic zeolite catalyst is a known process. Isoolefins or isoalkenes in this invention are those having the formula $R_2C=CH_2$ or $R_2C=CHR$, particularly $C_4$–$C_7$ isoolefins. Alkanols which may be used in the present invention include methanol, ethanol, 1-propanol, 2-propanol, 1-butanol and 2-butanol. Anhydrous methanol is a preferred alkanol. The term lower alkyl refers to $C_1$–$C_4$ alkyl including methyl, ethyl, n-propyl and isopropyl.

In the etherification process it is known that alkanol and iso-olefins may be reacted in equimolar quantities or either reactant may be in molar excess to influence the complete conversion of the other reactant. Because etherification is an incomplete reaction the etherification effluent comprises unreacted alkanol and unreacted hydrocarbons. On a stoichiometric equivalency basis, equimolar quantities of methanol and iso-olefins are advantageous but an excess between 2 and 200% of either component can be passed to the etherification reaction unit. In the present invention, the molar ratio of alkanol to iso-olefin, such as methanol to isobutylene, can be between 0.7 and 2, but preferably the molar ratio is 1 for methanol to isobutylene in liquid phase etherification. Advantageously, the excess methanol may be about 40% or more when the hydrocarbon feedstream comprises significant quantity of isoamylenes, but equimolar quantities are preferred when the hydrocarbon feedstream isoolefin component consists essentially of $C_4$ hydrocarbons.

The etherification conditions useful in the present invention for either $C_4+$ or $C_5+$ feedstreams containing isoalkenes, or isoolefins, include temperature between about 100° and 500° F., pressure between about 100 and 1000 psig, hydrocarbon feed rate between about 0.1 and 10 weight hourly space velocity (WHSV) based on catalyst, and hydrogen flow rate between about 10 and 2000 SCF/Bbl. Preferably, the etherification conditions comprise temperature of about 150°–400° F., pressure of about 200–600 psig, hydrocarbon feed rate of about 0.5–5 weight hourly space velocity (WHSV) based on catalyst.

$C_5+$ FCC olefinic gasoline is a preferred hydrocarbon feedstock for the etherification process employed in this invention, although isoolefin rich $C_4$ or $C_4+$ hydrocarbon streams can be used. Typically, FCC gasoline comprises predominantly $C_5$–$C_7$ hydrocarbons containing about 25% etherifiable isoolefins, particularly isoamylenes. Dienes are also present in FCC gasoline and are known to contribute to catalyst deactivation in prior art etherification processes. Small quantities of alpha olefins may also be present. The feedstream also contains traces of heteroatoms such as nitrogen and sulfur and basic nitrogen compounds such as acyclic amines in quantities sufficient to influence the rate of catalyst aging.

The catalysts useful in the olefin conversion and etherification processes to which the invention applies as described herein contain a zeolite sometimes referred to as medium pore zeolite, such as metallosilicate ZSM-5 type. It is preferred to use a medium pore shape selective acidic metallosilicate zeolite selected from the group consisting of ZSM-5, ZSM-11, ZSM-12, ZSM-22, ZSM-23, ZSM-35, ZSM-50, MCM-22, as well as larger pore zeolite Y and zeolite Beta. Acidic zeolite Beta is the preferred zeolite for etherification. ZSM-5 is more particularly described in U.S. Reissue Pat. No. 28,341 (of original Pat. No. 3,702,886), the entire contents of which are incorporated herein by reference.

ZSM-11 is more particularly described in U.S. Pat. No. 3,709,979, the entire contents of which are incorporated herein by reference.

Zeolite ZSM-12 is described in U.S. Pat. No. 3,832,449, to which reference is made for the details of this catalyst.

ZSM-22 is more particularly described in U.S. Pat. No. 4,046,859, the entire contents of which is incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

Zeolite ZSM-50 is described in U.S. Pat. No. 4,640,829, to which reference is made for details of this catalyst.

Zeolite Beta is described in U.S. Reissue Pat. No. 28,341 (of original U.S. Pat. No 3,308,069), to which reference is made for details of this catalyst.

MCM-22 is more particularly described in U.S. Pat. No. 4,954,325, the entire contents of which are incorporated herein by reference.

Zeolite Y is described in U.S. Pat. No. 3,130,007, to which reference is made for details of this catalyst.

The original cations associated with zeolites utilized herein can be replaced by a wide variety of other cations according to techniques well known in the art, e g., by ion-exchange. Typical replacing cations include hydrogen, ammonium, alkylammonium and metal cations, and their mixtures. Metal cations can also be introduced into the zeolite. In the case of metal cations, particular preference is given to metals of Groups IB to VIIIA of the Periodic Table, including, by way of example, iron, nickel, cobalt, copper, zinc, palladium, calcium, chromium, tungsten, molybdenum, rare earth metals, etc. These metals can also be present in the form of their oxides.

The zeolite catalyst is converted to the hydrogen form prior to use in the process of this invention. Although the process of this invention extends the active useful life of the catalyst, eventually after extended use in the process of this invention the catalyst will require regeneration to restore activity. This may be effected with hydrogen gas at elevated temperature. Optionally, the catalyst can be regenerated or reactivated oxidatively by treatment with air or oxygen to combust and remove carbonaceous deposits. Also, combinations of oxidative regeneration and regeneration by hydrogen gas can be used.

Referring now to the preferred application of the instant invention comprising the removal of conjugated dienes from olefinic hydrocarbon feedstreams to etherification processes, it has been discovered that these dienes can be effectively removed by the application of Diels-Alder chemistry to the hydrocarbon feedstock. The Diels-Alder reaction is well known to those skilled in the art of organic chemistry and consists in the 1,4-addition of an alkene or acetylenic linkage (dienophile) to a conjugated diene system (diene). Usually, the dienophile contains an electronegative group in conjugation with the alkene or alkyne bond. (See Advanced Organic Chemistry, E. Royals, Prentice-Hall, pp 407–411). The conjugated diene may be any $C_4+$ acyclic or cyclic diene.

Representative dienes found in $C_4+$ or $C_5+$ olefinic hydrocarbons streams include those having the structure:

$$R_1CH=CH-CH=CHR_2 \qquad (I)$$

where $R_1$ and $R_2$ can be hydrogen, alkyl, aryl or aralkyl, alike or different. Also, the term dienes includes cyclic and heterocyclic dienes such as cyclopentene and thiophene which are found in olefinic hydrocarbon feedstreams.

The dienophiles useful in the present invention include all those having the structure:

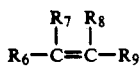

$$\begin{array}{c} R_7 \;\; R_8 \\ |\;\;\;\;| \\ R_6-C=C-R_9 \end{array} \qquad (II)$$

where at least one of $R_6$, $R_7$, $R_8$ and $R_9$ is an electronegative group and the remaining groups are hydrogen, alkyl, alkenyl, alkynalkyl, aryl or aralkyl. The electronegative groups useful in the dienophiles of structure (II) include:

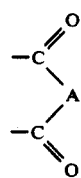

where A is O, NH, NR where R is alkyl;

where Z is H, OH, NH$_2$, halogen, alkyl, aryl, benzyl; and groups such as —CN, —NO$_2$, aryl, benzyl, —CH$_2$CN, —CH$_2$X where X is halogen

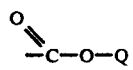

where Q is alkyl, aryl or benzyl. Dienophiles of particular use in the instant invention include maleic anhydride, maleimide, acrylonitrile, styrene, 4-carboethoxystyrene, ethyl acrylate, acrylamide, acrolein, methyl vinyl ketone, phenyl vinyl ketone, cinnamyl chloride, 4-sulfamylstyrene, methacrylic acid, ethyl vinyl carbonate, 2-hydroxyethyl acrylate, quinones and the like.

For the process of the present invention the preferred dienophile is maleic anhydride.

It is known that the formation of Diels-Alder adducts proceeds rapidly under moderate conditions, typically between 0° C. and 200° C., but usually between 20° C. and 100° C. The yield of adduct can be quantitative. The reaction is reversible, depending upon the structure of the diene and the dienophile.

To illustrate the process of the present invention and its advantages over prior art methods to remove dienes from olefinic hydrocarbon feedstock used for etherification of isoolefins catalyst aging experiments were conducted as presented in Examples 1–3. The feed is a light FCC gasoline, a C$_5$–C$_6$ distillation cut from a refinery FCC product stream.

EXAMPLE 1

The feed is water washed to lower nitrogen impurities. The feed is then blended 3:1 on a weight basis with dry methanol and placed into an autoclave with 1 gram of zeolite Beta for each 90 grams of light FCC gasoline. The sealed autoclave contents are allowed to react at autogeneous pressure and about 180° F. for 24 hours. At the end of each 24 hour period, the feed is replaced and the reaction product is analyzed. This method uses successive batch reactions to approximate running a fixed bed at weight hourly space velocity (WHSV) of 5 based on gasoline.

EXAMPLE 2

An identical and parallel etherification experiment is run except that the light FCC gasoline is first pretreated with maleic anhydride by reacting 2.0 grams of MA per 100 grams of light FCC gasoline in an autoclave at autogenous pressure and about 230° F. for about 12 hours. Excess MA is removed by filtration. GC analysis of the treated feed indicates the complete disappearance of all known diene peaks. NMR analysis of the treated feed confirms the presence of mixed alkyl substituted tetrahydrophthalic anhydride in about 3 wt % concentration. Since excess maleic anhydride is used in the pretreatment the product is saturated with respect to MA. This value is estimated by NMR to be about 0.1 wt %.

The FIGURE compares the aging data obtained from the different feed pretreatment conditions. Zeolite Beta is quickly poisoned by the untreated diene containing feed. After about 50 hours on stream there is more than a 20% differential in isoamylene conversion rate. However, the catalyst is substantially stabilized by maleic anhydride pretreatment.

An important discovery and advantage of the present process using maleic anhydride to form an adduct with dienes in olefinic hydrocarbon feedstock is that basic nitrogen compounds are also removed. These compounds react with MA or with the tetrahydrophthalic anhydride adduct to form amides or salts which are therefore effectively removed as catalyst deactivating agents in the process. One skilled in the art will understand that other dienophiles besides MA can be used to achieve this double effect in eliminating catalyst deactivating agents. Any acid or anhydride dienophile can function to remove basic nitrogen compounds in addition to forming an adduct with dienes and thereby remove both catalyst deactivating agents from the feedstream. However, MA is the preferred dienophile in this regard.

One of the significant features of the process of the invention is the fact that the treated feedstock containing the diene/dienophile adduct can be subjected to etherification of isoolefins in the feedstock without separation of the adduct. The adduct is carried through the etherification step into the reaction effluent. Separation of the effluent by means well known in the art such as distillation produces a gasoline boiling range product stream that contains both alkyl tertiary alkyl ethers and adduct which, in the case of MA, is tetrahydrophthalic anhydride or alkyl substituted derivatives thereof. The final gasoline boiling range product can also contain reaction products of the anhydride adduct or MA with alkanol that occurs during the etherification step or the product may contain unconverted MA. Alkanol can react with the alkyl tetrahydrophthalic anhydride adduct during the etherification step to produce the monoalkyl ester of the adduct. Depending on etherification conditions, the dialkyl ester of the adduct can also be formed.

It is a matter of considerable surprise and novelty in the present invention that the tetrahydrophthalic anhydride adducts prepared as described above in a gasoline boiling range hydrocarbon mixture result in a unique composition that displays both high octane value as well as supplementing the oxygen content of the gasoline. Considering the relatively high molecular weight of these adducts, the fact that they fall within the useful range of gasoline components, albeit at the high end, is unexpected; however, even more unexpected is the fact that they produce blending research octane numbers (RON) and motor octane numbers (MON) in the eighties.

The following Example 3 presents the results of an investigation into the properties of the tetrahydrophthalic anhydrides formed in the novel process of the invention.

EXAMPLE 3

Eight (8) gallons of light FCC gasoline are treated with MA according to the process described in Example 2. The MA treated FCC is distilled to provide 95% overhead and 5% bottoms. The overhead consists of diene free FCC. About 50 wt % of the bottoms consists of a separate, dense phase comprising concentrated mixed anhydrides resulting from the reaction of $C_5$-$C_6$ dienes with MA to form mixed alkyl substituted tetrahydrophthalic anhydrides. This product is an oil soluble up to eight weight percent in light FCC gasoline and miscible in para-xylene. The anhydrides contain almost 30 weight percent oxygen.

Table 1 lists the properties of the light FCC gasoline feed, the total reaction product with maleic anhydride, the concentrated mixed tetrahydrophthalic anhydrides, and diene-free light FCC gasoline product.. The process added 0.7 wt percent oxygen to light FCC gasoline while selectively removing dienes.

TABLE 1

| | PPM N | Wt. % S | RON | MON | Wt. % O | RVP |
|---|---|---|---|---|---|---|
| Light FCC Feed | 8 | .022 | 94.2 | 81.1 | NA | 12.5 |
| MA treated FCC Product | 8 | .021 | 94.0 | 81.4 | 0.7 | 12.6 |
| Conc. Mixed anhydrides | 53 | .038 | 84 | 81.1 | 26 | NA |

TABLE 1-continued

| | PPM N | Wt. % S | RON | MON | Wt. % O | RVP |
|---|---|---|---|---|---|---|
| Product (a) Diene free Light FCC Product (b) | 5 | .018 | 93 | 80.4 | NA | 12.3 |
| Hydrocarbon Products (c) | 5 | .064 | 91.6 | 79.0 | NA | NA |

Notes pertaining to Table 1:
(a) $C_5$-$C_6$ dienes react with MA to form mixed alkyl tetrahydrophthalic anhydrides;
(b) The MA treated FCC was distilled to 95% overhead and 5% bottoms. This material (b) is the overhead. The concentrated mixed anhydrides were a seperate, dense phase comprising about 50 wt % of the bottoms;
(c) The MA treated FCC was distilled to 95% overhead and 5% bottoms; the bottoms separated into two phases - a dense phase of concentrated mixed anhydrides and a less dense phase predominantly comprised of $C_6$+ light FCC gasoline; this material is called the hydrocarbon phase.

The product analysis depicted in Table 1 provides evidence that the forgoing treatment of light FCC gasoline, in addition to removing dienes, is removing nitrogen. The concentrated anhydrides are greatly enriched in nitrogen. The nitrogen removal percent is further confirmed by the composition of the diene free feed. Nitrogen has been reduced from about 8 ppm to about 5 ppm.

Pretreating olefinic gasoline with MA provides a method for removing dienes and basic nitrogen from refinery feedstock and could replace the current hydrotreater, stripper and water washing equipment currently used to remove these catalyst poisons in etherification processes. The reaction is stoichiometric, selective, non-catalytic and run at low temperatures. The products, tetrahydrophthalic anhydrides, are high octane, high oxygen content, low volatility gasoline or diesel components.

Although the Examples presented herein describe the treatment of light FCC gasoline feedstock for etherification, the process can be applied to any refinery feedstock containing dienes as an alternative to other methods to remove dienes such as hydrogenation. MA pretreatment can also be integrated with downstream paraffin alkylation and olefin skeletal isomerization for process improvements.

While the invention has been described by reference to specific embodiments there is no intent to limit the scope of the invention except as described in the following claims.

What is claimed is:

1. A process for improving catalyst life in olefinic hydrocarbon feedstream conversion processes carried out in contact with solid acid etherification catalyst particles, wherein said hydrocarbon feedstream contains catalyst deactivating amounts of diene, comprising:

treating said feedstream with at least one dienophile under reaction conditions sufficient to form an adduct of said diene and dienophile whereby a reaction product is produced comprising said olefinic hydrocarbon feedstream containing a substantially lower amount of said diene and catalyst life in said conversion processes is enhanced.

2. The process of claim 1 wherein said hydrocarbon conversion process comprises olefin etherification.

3. The process of claim 1 wherein said hydrocarbon conversion process comprises olefin oligomerization.

4. The process of claim 1 wherein said hydrocarbon conversion process comprises olefin skeletal isomerization.

5. The process of claim 1 wherein said catalyst particles comprise acidic shape selective metallosilicate catalyst particles.

6. The process of claim 5 wherein said catalyst comprises aluminosilicate.

7. The process of claim 6 wherein said catalyst is selected from the group consisting of ZSM-5, ZSM-11, ZSM-12, ZSM-23, ZSM-35, ZSM-48, MCM-22 and zeolite Beta.

8. The process of claim 1 wherein said dienophile comprises maleic anhydride.

9. The process of claim 1 wherein said hydrocarbon feedstream also contains basic nitrogen whereby both diene and basic nitrogen are removed from said feedstream.

10. The process of claim 1 wherein said dienophile has the structure:

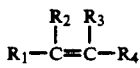

where $R_1$ is an electronegative group and where $R_2$, $R_3$ and $R_4$ are hydrogen, alkyl, alkenyl, alkynalkyl, aryl or aralkyl.

11. The process of claim 10 wherein said electronegative group is selected from the group consisting of

where Z is H, OH, $NH_2$, halogen, alkyl, aryl, benzyl —CN, —$NO_2$, aryl, benzyl, —$CH_2CN$, —$CH_2X$ where X is halogen;

where Q is alkyl, aryl and benzyl.

12. The process of claim 1 wherein said olefinic hydrocarbon feedstream comprises $C_4+$ or $C_5+$ olefinic gasoline boiling range hydrocarbons.

13. The process of claim 1 wherein said reaction conditions comprise temperature between 0° C. and 200° C.

14. A process for the production of $C_5+$ gasoline boiling range hydrocarbons rich in alkyl tertiary alkyl ethers from a $C_5+$ olefinic hydrocarbon feedstream rich in isoolefins and containing catalyst deactivating amounts of dienes, said process comprising:

contacting said $C_5+$ feedstream with at least one dienophile under reaction conditions sufficient to form the adduct of said diene and said dienophile whereby a reaction product is produced comprising said olefinic hydrocarbon feedstream containing a substantially lower amount of said diene; and contacting at least a portion of said reaction product and an alkanol feedstream with acidic etherification catalyst under isoolefin etherification conditions whereby an effluent stream is produced comprising unconverted $C_5+$ hydrocarbons, unconverted alkanol, said adduct and said alkyl tertiary alkyl ether.

15. The process of claim 14 wherein said feedstream comprises $C_5+$ hydrocarbons rich in isoamylene and said alkanol comprises methanol whereby said effluent contains tertiary amyl methyl ether (TAME).

16. The process of claim 14 wherein said feedstream comprises $C_4+$ olefinic hydrocarbon feedstream rich in isoolefins and containing catalyst deactivating amounts of dienes.

17. The process of claim 14 wherein said dienophile comprises maleic anhydride and said effluent contains high octane value alkyl substituted tetrahydrophthalic acid ester and/or anhydride adduct, and wherein said olefinic hydrocarbon feedstream contains basic nitrogen compounds which are removed by said maleic anhydride.

18. The process of claim 14 wherein said alkanol is selected from the group consisting of methanol, ethanol, 1-propanol, 2-propanol, 1-butanol and 2-butanol.

19. The process of claim 14 wherein said reaction conditions comprise temperature between 0° C. and 200° C.

20. The process of claim 14 wherein said dienophile has the structure:

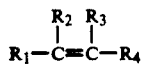

where $R_1$, is an electronegative group and where $R_2$, $R_3$, and $R_4$ are hydrogen, alkyl, alkenyl, alkynalkyl, aryl or aralkyl.

21. A composition comprising high octane value gasoline having an enhanced oxygen content, said composition comprising $C_5+$ gasoline boiling range hydrocarbons containing alkyl substituted tetrahydrophthalic anhydride or $C_1$-$C_4$ esters thereof.

22. A composition comprising an etherificastion effluent which contains high octane value gasoline having an enhanced oxygen content, said composition comprising the reaction product of a process comprising:

contacting a $C_5+$ feedstream comprising $C_5+$ gasoline boiling range hydrocarbons containing at least one diene hydrocarbon with a dienophile comprising maleic anhydride under reaction conditions sufficient to form the adduct of said diene and said dienophile, said adduct comprising alkyl substituted tetrahydrophthalic anhydride, whereby a reaction product is produced comprising said olefinic hydrocarbon feedstream containing a substantially lower amount of said diene; and contacting said reaction product and an alkanol feedstream with acidic etherification catalyst under isoolefin etherification conditions whereby the effluent stream is produced comprising unconverted $C_5+$ hydrocarbons, unconverted alkanol, said adduct and said alkyl tertiary alkyl ether.

23. The composition of claim 22 wherein said alkanol comprises methanol.

24. In the process for the production of $C_5+$ gasoline boiling range hydrocarbons rich in alkyl tertiary alkyl ethers comprising contacting a hydrocarbon feedstream and $C_1$-$C_4$ alkanol with acidic etherification catalyst under etherification conditions whereby said hydrocarbons rich in alkyl tertiary alkyl ethers are produced, said hydrocarbon feedstream comprising $C_5+$ olefinic hydrocarbons rich in isoolefins and containing catalyst deactivating amounts of dienes and basic nitrogen compounds, the improvement comprising:

pretreating said feedstream with maleic anhydride under reaction conditions sufficient to form the adduct of said diene and said maleic anhydride, said adduct comprising alkyl substituted tetrahydrophthalic anhydride, whereby a reaction product is produced comprising said olefinic hydrocarbon feedstream containing a substantially lower amount of said catalyst deactivating diene and a substantially lower amount of said basic nitrogen.

25. The process of claim 24 wherein said catalyst particles comprise solid acid ion exchange resin catalyst.

26. The process of claim 25 wherein said catalyst comprises high molecular weight sulfonated resin.

27. The process of claim 1 wherein said feedstream contains thiophene whereby treating with said dienophile lowers the thiophenic sulfur content of said product 28. The process of claim 1 including the further step of separating said reaction product by distillation and recovering an overhead stream which is substantially free of dienes.

29. The process of claim 28 wherein said feedstream contains thiophene and the sulfur content of said overhead is substantially lower than said feedstream.

30. A high octane fuel composition for motor gasoline use comprising: a major amount of $C_5+$ gasoline boiling range hydrocarbons; an octane-enhancing amount of lower alkyl tert-alkyl ether, and alkyl-substituted tetrahydrophthalic anhydride or $C_1$-$C_4$ esters of said anhydride.

31. A high octane fuel composition according to claim 30 wherein said ether is an etherification product of $C_1$-$C_4$ lower alkanol and tertiary-amylene; and wherein said anhydride is an adduct reaction product of maleic anhydride and conjugated diene.

32. A high octane fuel composition according to claim 31 wherein said ether comprises tertiary-amyl methyl ether; and wherein said anhydride is an adduct reaction product of maleic anhydride and pentadiene, whereby catalyst-deactivating amounts of diene and basic nitrogen compounds are removed from said composition.

33. A high octane fuel composition comprising: $C_5+$ gasoline boiling range hydrocarbon, an octane-enhancing amount of lower alkyl ether, and an adduct reaction product of at least one dienophile and conjugated diene, said fuel composition being substantially free of unreacted diene.

34. A high octane fuel composition according to claim 33 wherein said ether comprises tertiary-amyl methyl ether; and wherein the adduct is a reaction product of maleic anhydride with pentadiene.

* * * * *